United States Patent [19]

Bax et al.

[11] 4,331,159
[45] May 25, 1982

[54] ELECTROCARDIOGRAPHIC STORAGE SYSTEM USING A ROTATING FILM DRUM

[75] Inventors: Ronald F. Bax, Columbia; John H. Perry, Silver Spring, both of Md.

[73] Assignee: Pfizer Inc., New York, N.Y.

[21] Appl. No.: 108,830

[22] Filed: Dec. 31, 1979

[51] Int. Cl.³ .............................................. A61B 5/04
[52] U.S. Cl. ............................... 128/710; 346/33 ME
[58] Field of Search ..................... 128/696, 708, 710; 346/33 ME

[56] References Cited

U.S. PATENT DOCUMENTS

| 2,539,009 | 1/1951 | Chaney et al. | 346/138 |
|---|---|---|---|
| 2,718,224 | 9/1955 | Apstein | 128/710 |
| 2,976,108 | 3/1961 | Johnson | 346/109 |
| 3,011,856 | 12/1961 | Palmer et al. | 346/109 |
| 3,020,119 | 2/1962 | Marchal et al. | 346/33 ME |
| 3,339,543 | 9/1967 | Richard | 128/712 |
| 3,590,811 | 7/1971 | Harris | 128/708 |
| 3,853,119 | 12/1974 | Peterson et al. | 128/711 |
| 3,893,453 | 7/1975 | Goldberg et al. | 128/710 |
| 3,951,135 | 4/1976 | Goldberg et al. | 128/710 |
| 4,051,482 | 9/1977 | Andresen | 128/710 |

*Primary Examiner*—William E. Kamm
*Attorney, Agent, or Firm*—Cushman, Darby & Cushman

[57] ABSTRACT

A system and method for visually recording an ECG signal in a helical track about a cylindrical record. The "R" wave of each heart beat is detected and utilized to synchronize the first recorded heart beat pulse of each line. Imaging on the record is by optical exposure of a photographic recording medium.

25 Claims, 6 Drawing Figures

ELECTROCARDIOGRAPHIC STORAGE SYSTEM USING A ROTATING FILM DRUM

BACKGROUND AND SUMMARY OF THE INVENTION

This invention relates in general to the display of electrocardiograph (ECG) signals and more specifically to apparatus and methods for displaying such signals accumulated over a substantial monitoring time. Even more specifically, this invention is directed to methods and apparatus for presenting large volumes of ECG data in a compact visual form.

The fundamental problem associated with the long term ECG monitoring of a patient is that a large volume of data, once taken from the patient, is not readily usable by a cardiologist. This data is often collected on a roll or a cassette of magnetic tape and requires special equipment for playback. Even if the special equipment is available, it is still inconvenient for the cardiologist to examine the data quickly.

For this reason, systems for displaying data taken over an 8-10 hour period in a compact and easily readable form are highly advantageous. U.S. Pat. Nos. 3,893,453 and 3,951,135 issued to Goldberg et al. on July 8, 1975 and Apr. 20, 1976 respectively, teach a rotating drum system for recording a large volume of ECG information. These patents generally recognize the fundamental problem presented to a cardiologist attempting to analyze ECG signal data obtained over a long monitoring period. The Goldberg et al solution to this display problem is to record the continuous ECG signal in a helical fashion about a cylindrical record member which is then slit and/or opened along a line to present a flat picture of the collected ECG signals. In the Goldberg system, the speed of the rotating drum is varied in proportion to the patient's heart rate. Thus, all heart beats, as recorded on the drum, appear to have the same horizontal span. There is no discernable distinction between a row of ECG pulses responsive to a heart rate of a 120 beats per minute and a row of pulses responsive to a heart rate of 80 beats per minute. In order to interpret pulse rate information in the Goldberg et al system, some sort of time base marker would have to be recorded along with the ECG signals as an interpretation aid. In addition, at a high pulse rate the Goldberg type system utilizes film at a high rate. Thus, contrary to what is taught in the Goldberg et al system, it would be useful for the display to maintain a uniform time base so that differences in pulse rate will be readily discernable.

There is additional advantage in being able to synchronize the pulses on successive tracks of the helical trace produced on the drum. An ECG signal related to a heart beat contains a plurality of "waves": P, QRS, T and U. For diagnostic purposes, cardiologists find it most easy to view the mass of display data when each of a particular wave type on a track of the helical trace is synchronized with corresponding waves on adjacent tracks, e.g., the "R" wave of each heartbeat on each line of the trace lines up with the corresponding "R" waves of heartbeats appearing on the other lines of the trace. A display that is so synchronized allows a cardiologist to readily be apprised of irregularities occurring within and among the various heartbeats recorded.

The system and method of displaying ECG data according to the present invention specifically addresses this synchronization problem. The system continuously records the ECG signal in a helical trace about a cylindrical record using a photographic process, producing a "hard copy" of the ECG trace, easily read by a cardiologist. In a similar fashion to the Goldberg patent, the cylindrical record, once having been completed, is opened into a flat record along a reference or index line thus presenting the cardiologist with a two dimensional picture that may be rapidly scanned for pulses which do not clearly fit within an otherwise regular pattern of recorded pulses.

In the present invention, the cylindrical record turns a fixed angular distance at a predetermined rate of rotation, when triggered by an ECG waveform. An "R" wave detector set to a predetermined threshold, detects the presence of the "R" wave component of a heartbeat and triggers a one shot providing a signal having a predetermined period, suitably 200 msec. The signal from the one shot activates a stepper motor drive providing drive pulses to a stepper motor mechanically coupled to the cylindrical record.

Thus, upon detection of the "R" wave, the record turns for 200 msec. to capture the most significant portion of a heartbeat signal. The record then stops until the next "R" wave again triggers the cylindrical record. To ensure that each "R" wave aligns with the wave in the other lines of the trace, synchronizing means are provided so that the first recorded wave in each successive line of recording begins at a common reference or index line. A position sensor optically senses the presence of the reference or index line to provide a reference for "R" wave triggering on each successive track. With this system, aberrant heartbeats represent flaws in an otherwise regular pattern.

A further improvement of the present invention is the means for recording on the readable trace. The somewhat clumsy pen and ink recording system found in previous devices is eliminated. In its place, a digital, photographic recording process is used.

The photographic recording process includes means for converting the electrical signals at input electrodes into optical signals focused at the surface of the cylindrical record. An analog ECG signal at the input electrodes is sampled at a sufficient rate to insure no loss of signal definition and the samples are converted into digital serial data. The digital serial data is demultiplexed into a plurality of address lines for coupling to a linear array of light emitting diodes (LEDs). The LED array is arranged so that a digital signal on a particular address line will light a predetermined one of the LEDs. Optical fibers couple each of the LEDs to a lens system having a focus at the surface of the record. The lens system is mounted on a screw mechanism so that it is moveable in the axial direction of the cylindrical record. A belt/pulley arrangement driven by the rotation of the record drives the screw mechanism causing the lens system to move in the axial direction of the cylindrical record as the drum rotates. Thus, a helical photographic trace is formed on the record.

BRIEF DESCRIPTION OF THE DRAWINGS

Many of the attendant advantages of the present invention will be readily apparent as the invention becomes better understood by reference to the following detailed description when considered in conjunction with the appended claims and the accompanying drawings, wherein:

DETAILED DESCRIPTION OF THE PREFERRED EMBODIMENT

Figure 1:
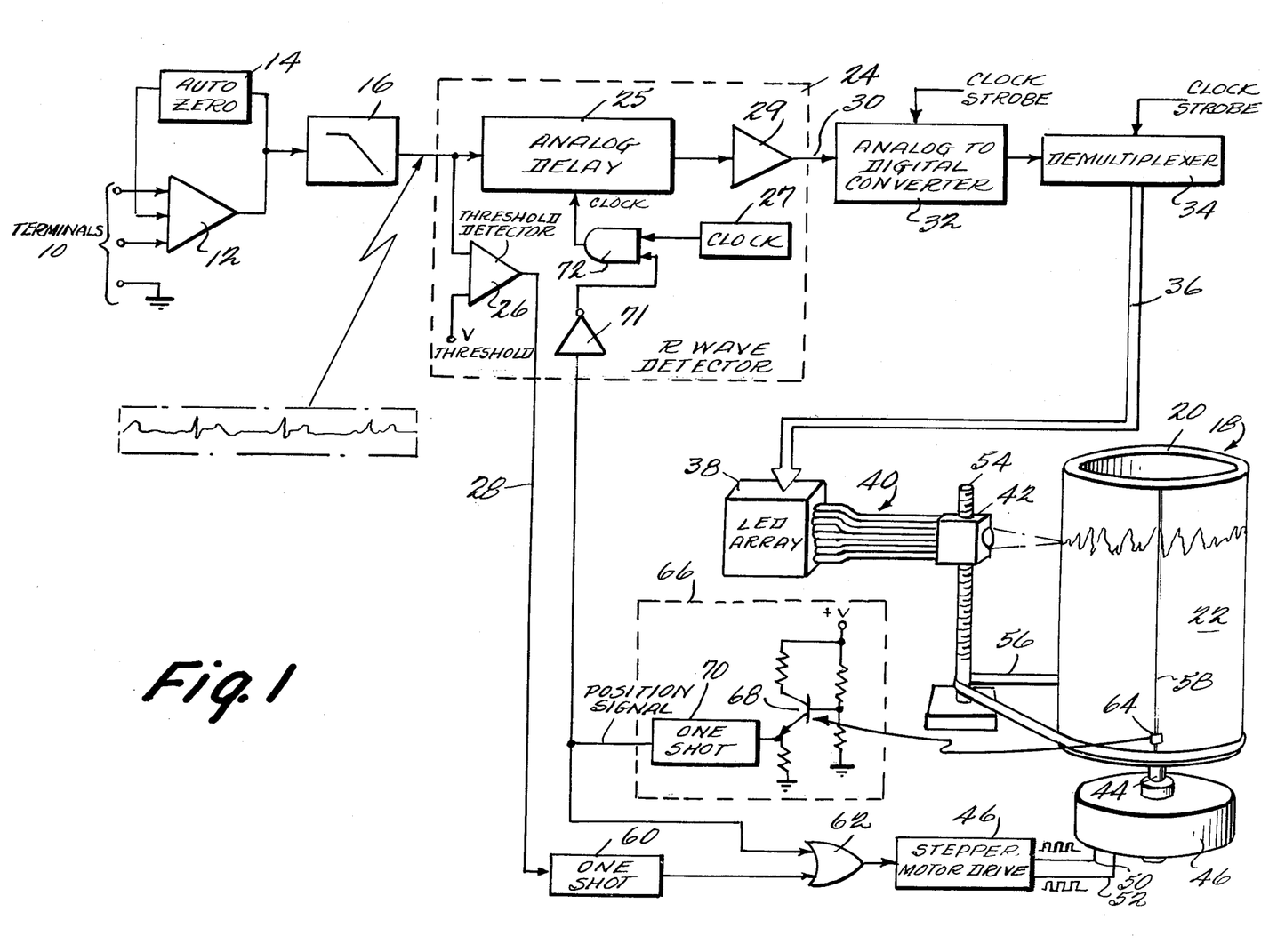
FIG. 1 is a general block, schematic, and pictorial diagram of the electrocardiographic storage system according to the present invention.

Referring now to the drawings, wherein like reference numerals designate like or corresponding parts throughout the several FIGURES and referring specifically to FIG. 1, there is shown a general block, schematic, and pictorial diagram of the electrocardiographic storage system according to the present invention. Terminals 10 are coupled to an electrical signal from a conventional electrocardiograph (ECG) apparatus (not shown) for sensing a patient's ECG response. Terminals 10 are coupled to an instrumentation amplifier 12 including a conventional automatic offset zeroing feedback loop 14. Instrumentation amplifier 12 is advantageously an LF 152 FET input instrumentation amplifier manufactured by National Semiconductor, or its equivalent.

The output signal from instrumentation amplifier 12 is an analog ECG signal related to the patient's cardiac activity and is coupled through a low pass filter 16 for filtering out high frequency noise which may be introduced through terminals 10.

At the output of low pass filter 16, the ECG signal has a waveform similar to that which appears on the trace of a conventional electrocardiograph apparatus wherein the trace is displayed on a cathode ray tube or on a paper roll chart. A portion of a normal electrocardiograph trace including P, "QRS" and T waves of each heart beat is shown in FIG. 1. The ECG signal appearing at the output of low pass filter 16 is ultimately recorded as a visually detectable pattern on a record member 18. Record member 18 includes a cylindrical drum 20 having a sheet of photographic paper 22 therearound.

The ECG signal is coupled through an "R" wave detector 24 which performs two separate and distinct functions for achieving synchronization of the heart beats recorded on record member 18. First "R" wave detector 24 provides a delay for the ECG signal passing therethrough. Secondly, "R" wave detector 24 detects a predetermined one of each of the "R" waves of the ECG signal.

As can be seen from the normal ECG trace in FIG. 1, the "R" wave is a sharp spike having a higher magnitude of signal level than the other ECG signal components. The threshold function of "R" wave detector 24 utilizes a threshold detector 26 set to trigger at a predetermined threshold level $V_{thresh}$. Threshold detector 26 provides a sync pulse on output line 28 of "R" wave detector 24 for use in triggering the onset of rotation of a record member 18.

The preferred embodiment employs an "R" wave detector. Obviously any device which detects any wave of the ECG signal may be substituted. Devices for detecting "R" waves and other waves are well known in the art and commercially available.

A second output signal line 30 from "R" wave detector 24 provides an ECG signal essentially identical to the signal inputted to the "R" wave detector, but delayed by approximately 10 milliseconds. It is this delayed ECG signal that is utilized to generate an optical image for ultimate photographic fixation of the ECG trace on record member 18.

The delay function of "R" wave detector 24 is provided by an analog delay 25 coupled to the output of low pass filter 16. Analog delay 25 can be a bucket-brigade or charge coupled analog delay, suitably an MN 3001 manufactured by Matsushita Electronics Corporation or the like. Analog delay 25 includes 512 stages of analog memory, each stage having a group of field effect transistors for memorizing an analog voltage level. A clock 27 steps the ECG signal through analog delay 25 to its output where the delayed ECG signal is coupled to an amplifier 29. Amplifier 29 provides amplification, level shifting and low pass filtering, suitably having a cut-off frequency of 5 KHz.

Output signal line 30 is coupled to the input of an analog to digital (A/D) converter 32 for converting the delayed ECG signal into digital data. A/D converter 32 is advantageously of the dual slope type because such a converter can be set to integrate for 1/60 second (16.67 milliseconds) so as to notch out extraneous 60 Hz. pickup. Additional 60 Hz. attenuation can be provided, if needed, by coupling a 60 Hz. notch filter between low pass filter 16 and "R" wave detector 24. Of course, A/D converter 24 can also be of the successive approximation type or charge-balancing type. The clock strobe required for the A/D converter, can be derived from clock 27 as should be apparent.

The output of A/D converter 32 is in the form of "digitized" data which is coupled to a demultiplexer 34. Demultiplexer 34 converts the digital data from A/D converter 32 into signals on a plurality of address lines 36. Address lines 36 are coupled to an array of light-emitting diodes (LEDs) 38 for generating an optical signal related to the delayed ECG signal. Again, the clock strobe, if required for the Demultiplexer 34 can be derived from clock 27 as should be apparent.

Associated with each LED is one end of an optical fiber, the group of which form a fiber optic bundle 40. The other end of each of the optical fibers within fiber optic bundle 40 is coupled to a lens system 42 for focusing the optical signal from the optical fibers onto record member 18.

It has been determined experimentally that 100 samples/sec of an analog ECG signal provides sufficient time detail for accurate diagnosis. In addition, a voltage (magnitude) resolution of 1 part in 100 is also acceptable. If 128 LEDs in a single row constitute array 38, each LED defining a pixel at the surface of film 34, each ECG trace line is 128 pixels high and record 18 can rotate at 100 pixels/sec. Each second will then contain 12,800 pixels of information (each hour will contain $4.608 \times 10^7$ pixels of information and 8 hours of recording will contain $3.6864 \times 10^8$ pixels of information. For a 4"×8" sheet of film 22, a single pixel would have a size of $8.68 \times 10^{-8}$ in$^2$).

Record member 18 is coupled via a shaft 44 to a stepper motor 46 so as to be rotated thereby. Stepper motor 46 is suitably one of the SLO-SYN stepping motors manufactured by Superior Electric.

Stepper motor 46 is driven by a stepper motor drive 48 which is suitably a stepper motor IC driver SAA 1027, manufactured North American Phillips Controls Corporation, Cheshire, Conn., or its equivalent. Stepper motor drive 48 generates pulses at its output signal lines 50 and 52 for controlling the rotational rate of stepper motor 46.

Lens system 42 is mounted on a threaded shaft 54 driven by a belt 56. Belt 56 causes shaft 54 to turn with the rotation of record member 18. As shaft 54 turns in response to the rotation of record member 18, lens system 42 moves parallel to the axis of rotation of record member 18. Thus, as record member 18 rotates, lens system 42 moves linearly and the optical focus of the lens system on the surface of the record member defines a helical trace.

The threading of shaft 54 and the size of the pulleys for belt 56 are chosen such that for each complete revolution of record 18, lens system 42 linearly displaces a sufficient amount so that adjacent lines of the helical trace will not overlap one another.

As stated, record member 18 includes a cylindrical drum 20 and a sheet of photographic film 22 wrapped around the drum. By wrapping a flat sheet of film 22 around the outer surface of drum 20, a seam 58 is defined where two ends of the film are joined.

The remaining circuitry to be described provides for synchronization among the various lines of the helical trace of the ECG signal recorded on record member 18.

If record 18 were permitted to rotate continuously and if ECG signals were recorded without interruption, the positioning of the ECG waves on each line would be random with respect to the other lines. The "R" waves of the first heart beats in each line would not necessarily line up with one another when film 22 was unwrapped from drum 20. Thus, there would be no regular pattern to the voluminous number of heart beats recorded, making it difficult to recognize subtle changes in the heart beat signal from line to line.

The present system solves this problem by synchronizing the initial heart beat (the "R" wave) of each line of the helical trace with the initial heart beat of every other line. Seam 58 is used to define a reference or index line. Each time this reference line has been traversed, the rotation of record member 18 is triggered on first "R" wave detected thereafter. Thus, the "R" waves of the initial heart beat of each line will be in alignment with one another when film 22 is removed from drum 20.

The output sync pulse on signal line 28 from "R" wave detector 24 is coupled to the input of a one shot 60, having a period of approximately 200 milliseconds. 200 milliseconds is sufficient time for the recording of the most significant components of an ECG signal related to one heart beat. The 200 milliseconds width pulse from one-shot 60 is coupled to one input of an OR gate 62, the output of which is coupled to the input of stepper motor drive 48. Thus, each time an "R" wave is detected by threshold detector 26 a sync pulse is generated on line 28 causing one shot 60 to be triggered. One shot 60, coupled through an OR gate 62, causes stepper motor drive 48 to produce output pulses for 200 milliseconds, thereby causing record member 18 to rotate for 200 milliseconds. After 200 milliseconds, record 18 stops and remains stopped until the next "R" wave triggers one shot 60 again.

However, the use of a sync pulse corresponding to an initial "R" wave alone may be insufficient to synchronize the first "R" wave of each line of the helical trace. The initial triggering on each line therefore preferably always takes place after seam 58 has been traversed and record member 18 is stopped.

A marker 64 is permanently attached at a fixed position on the outer surface of record 18 to provide a visible reference that can be optically detected to indicate that seam 58 is at the optical focus of lens system 42. A position sensor 66 optically senses the presence of marker 64 and provides a signal to OR gate 62. Position sensor 66 includes a photo transistor 68 biased so as to be optically sensitive to marker 64. The output of transistor 68 is coupled to a one-shot 70 for producing a logic level position signal having a predetermined period. The position signal from one shot 70 is coupled to the second input of OR gate 62. Thus, whenever a position signal appears at the output of one shot 70, stepper motor drive 48 will be triggered for a predetermined period of time based upon the period of one shot 70. The output of stepper motor drive 48, in turn, advances the rotation of motor 46 so that seam 58 is traversed. Once seam 58 has been traversed, the first "R" wave of the ECG signal will trigger normal recording rotation of record 18. In this manner, the first pulse on each line of the helical trace will be synchronized with the first pulse of every other line.

The function of analog delay 25 will now be apparent. The 10 millisecond delay induced by analog delay line 25 allows sufficient time for record 18 to accelerate up to its normal rotational rate for recording before data from A/D converter 32 is converted into an optical signal for recording. This prevents an initial time compression at the start of each recorded pulse. Furthermore, the delay can enable the recording of the "P" and "Q" waves which are recorded prior to the triggering of threshold detector 26.

During the rotation of record 18 in response to the position signal from position sensor 66, analog delay 25 is inhibited. Clock 27 is coupled to the clock input of analog delay line 25 through one input of an AND gate 72. An inverter 71 couples the output of one shot 70 (the position signal) to a second input of AND gate 72. Clock pulses are therefore coupled to analog delay 25 only when the position signal is not present. Thus, when a position signal appears at the output of one-shot 70, clock pulses are inhibited and the ECG signal is not clocked through analog delay 25.

An alternate arrangement for inhibiting the optical signal would be to gate output line 30 of "R" wave detector 24 during the presence of a position signal.

Thus, there is defined a method for storing an ECG signal. The ECG signal is delayed to form a delayed ECG signal. An optical signal is generated in response to the delayed ECG signal and is focused onto a record member. The presence of a predetermined wave of the ECG signal is determined and a sync signal is generated in response thereto. The rotation of the drum is triggered by the sync signal and continues for a predetermined time period and the optical signal is recorded on the record. A predetermined reference line position on the drum is sensed and a position signal is generated whenever that position is determined. In response to the position signal, the record is rotated so as to traverse the reference line while the recording of the optical signal is inhibited. In this manner, all lines of a helical trace of the ECG signal on the record are synchronized.

Figure 2:
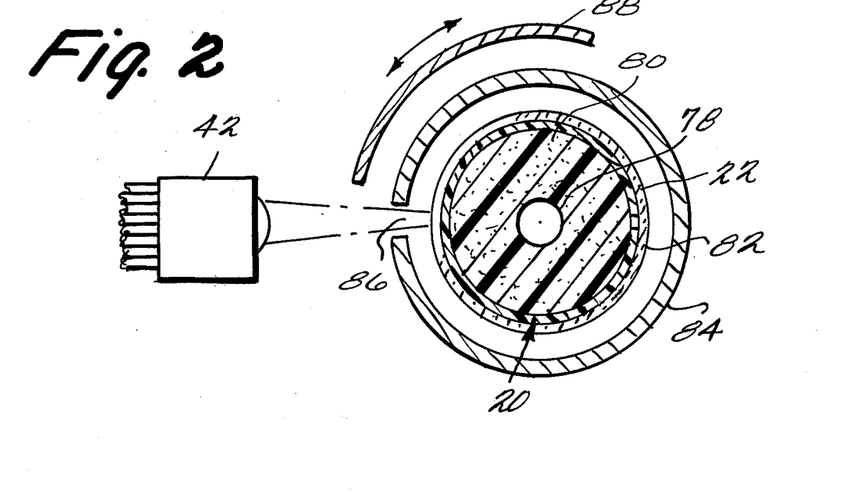
FIG. 2 shows cutaway side view of the record and recording mechanism.
Figure 3:
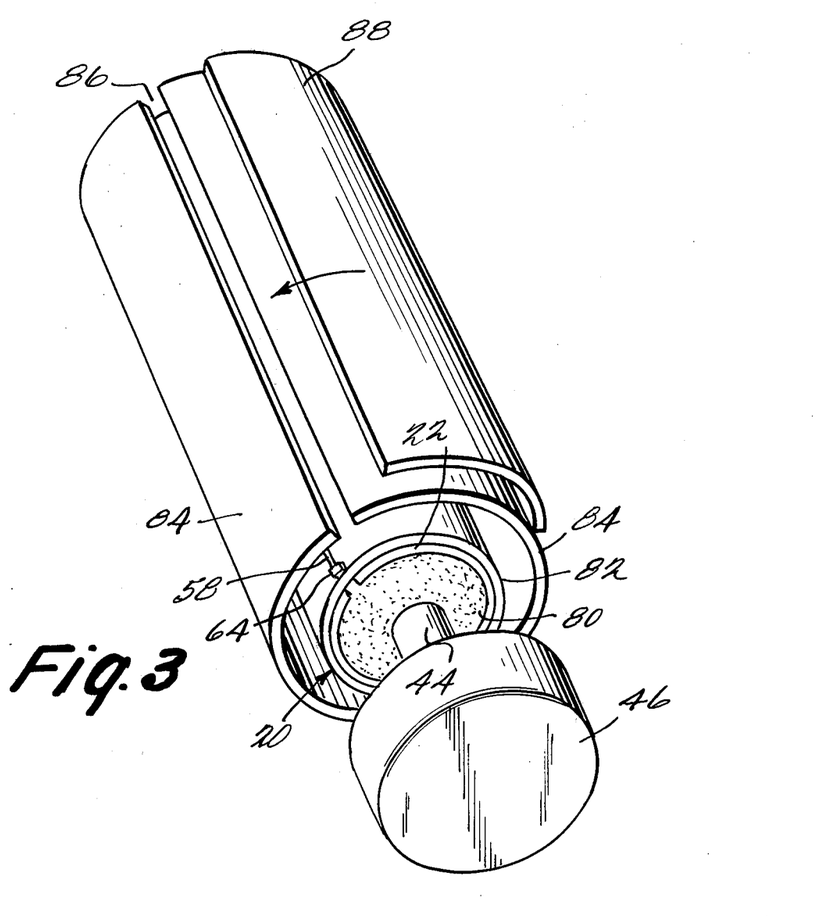
FIG. 3 shows a perspective view of the record and recording mechanism.

Referring now to FIGS. 2 and 3, cutaway side and perspective views of record member 18 are shown respectively. Cylindrical drum 20 includes a central member 78 suitably fabricated from a solid material, to which shaft 44 is coupled. Cylndrical drum 20 further includes a pliable member 80 suitably fabricated from a sponge-like material surrounding central member 78. Photographic film 22 is wrapped around pliable member 80 as tightly as possible with its photographically sensitive emulsion facing outwardly. The two ends of film 22 form seam 58, shown somewhat exaggerated in the figure. As previously stated, seam 58 becomes a reference index line at which each line of the helical trace is synchronized. A thin sheet of optically transparent material 82, suitably of clear plastic or glass is wrapped around film 22 and presses the film against pliable member 80. Thus, an outward force is exerted by pliable member 80 against film 22 in order to secure it tightly against sheet 82. This arrangement maintains film 22 relatively fixed during exposure by lens system 42. Record 18 is surrounded by a stationary light-tight cover 84 having a gap 86 therein for allowing free passage of optical signals from lens system 42 to the surface of film 22. In addition, a selectably movable gap cover 88 is provided as an additional measure of light tightness.

The LED array having a single column and 128 rows (128 elements) described with reference to FIG. 1 is only one of many possible array and demultiplexer alternatives that are possible. For example, different numbers of LED's can be provided, if desired.

Figure 4:
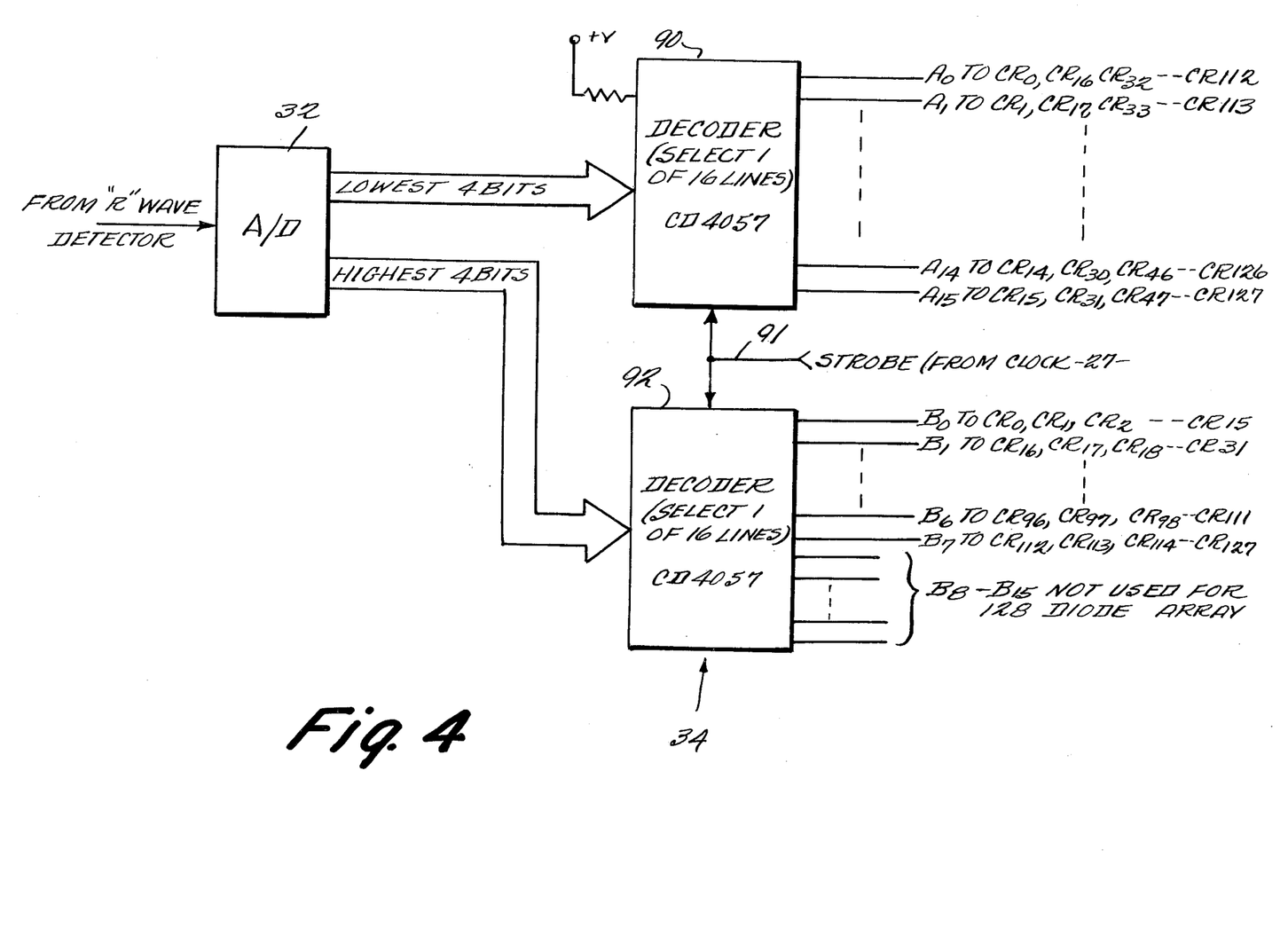
FIG. 4 is a more detailed block diagram of the demultiplexing scheme for an LED array including 128 diodes.
Figure 5:
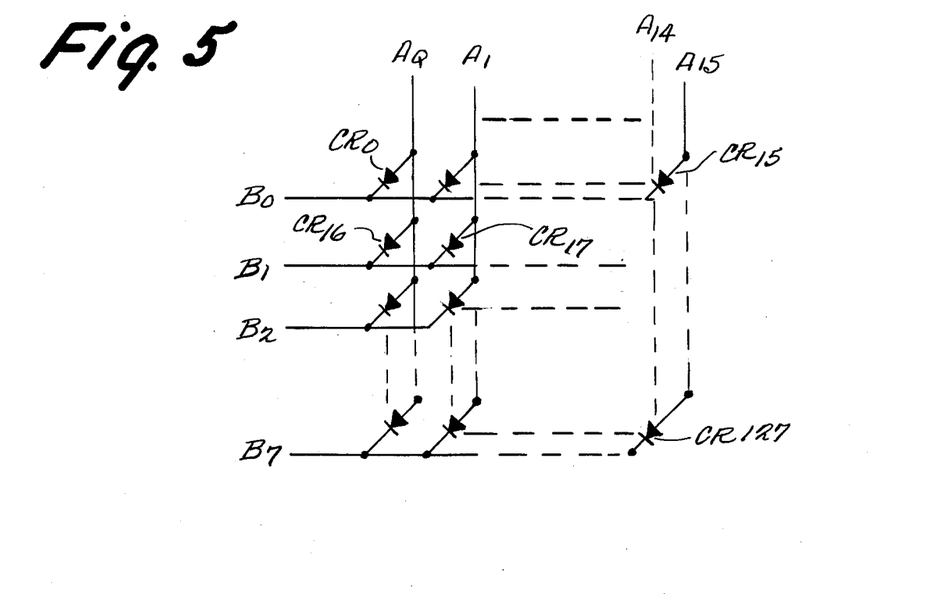
FIG. 5 is a schematic diagram of a 128 LED array.

Referring now to FIG. 4, there is shown a more detailed block diagram of a demultiplexer for an array of 128 LEDs arranged in sixteen columns and eight rows (the LED array is shown in FIG. 5).

The ECG signal from "R" wave detector 18 is a faithful reproduction of the ECG signal at the output of the "R" wave detector but delayed by 10 milliseconds. This output signal is used to generate optical signals for ultimate recording onto film 22. Demultiplexer 34 for a 128 LED matrix includes a pair of decoders 90 and 92 (CD 4057s or equivalent). The output lines from A/D converter 32 carrying the least significant four bits of information are coupled to decoder 90 while the output lines from the A/D converter carrying the most significant four bits of information are coupled to decoder 92. Decoders 90 and 92 are of the type wherein one of sixteen output lines is selected based upon a four-bit input. The output lines from decoder 90 become the column address lines (A) for the LED array and the outlines from decoder 92 become the row address lines (B) for the array. Decoders 90 and 92 are strobed from a common line 91. The sixteen output lines A0–A15 of decoder 90 and the first eight output lines B0–B7 of decoder 92 are coupled to the row lines of the LED array. In this particular example, lines $B_8$–$B_{15}$ of decoder 92 are not utilized.

Referring now to FIG. 5, there is shown a schematic diagram of an LED array for the particular example of 128 LEDs arranged in a matrix. Output line $A_0$ from decoder 90 is coupled to the anode of each of the LEDs in the first column, i.e., $CR_0$, $CR_{16}$, etc. Output line $A_1$ from decoder 90 is coupled to the anode of each of the LEDs in the second column, i.e., $CR_1$, $CR_{17}$, etc. Similarly, the output line $B_0$ from decoder 92 is coupled to the cathode of each of the LED elements in the first row, ie., $CR_0$, $CR_1$, etc. Output line $B_1$ of decoder 92 is similarly coupled to the cathode of each of the LED elements in the second row, i.e., $CR_{16}$, $CR_{17}$, etc. This scheme is fully developed to complete the entire array including 128 diodes.

As the optical fiber array shown includes 128 elements in a single physical (vertical) row, there is a single optical fiber associated with each of the LEDs in the 128 diode array. One end of each fiber optically coupled to a single LED and the other end of each fiber is coupled to lens system 42. The optical fiber ends associated with lens system 42 are arranged such that the vertical physical position (as seen in FIG. 1) of the point of light projected by the lens system corresponds to the magnitude of the ECG signal.

Other embodiments and modifications of the present invention will be apparent to those of ordinary skill in the art having the benefit of the teachings presented in the foregoing description and drawings.

Utilizing the basic scheme set forth above, various alternate means for synchronizing each line of the helical trace are apparent.

Figure 6:
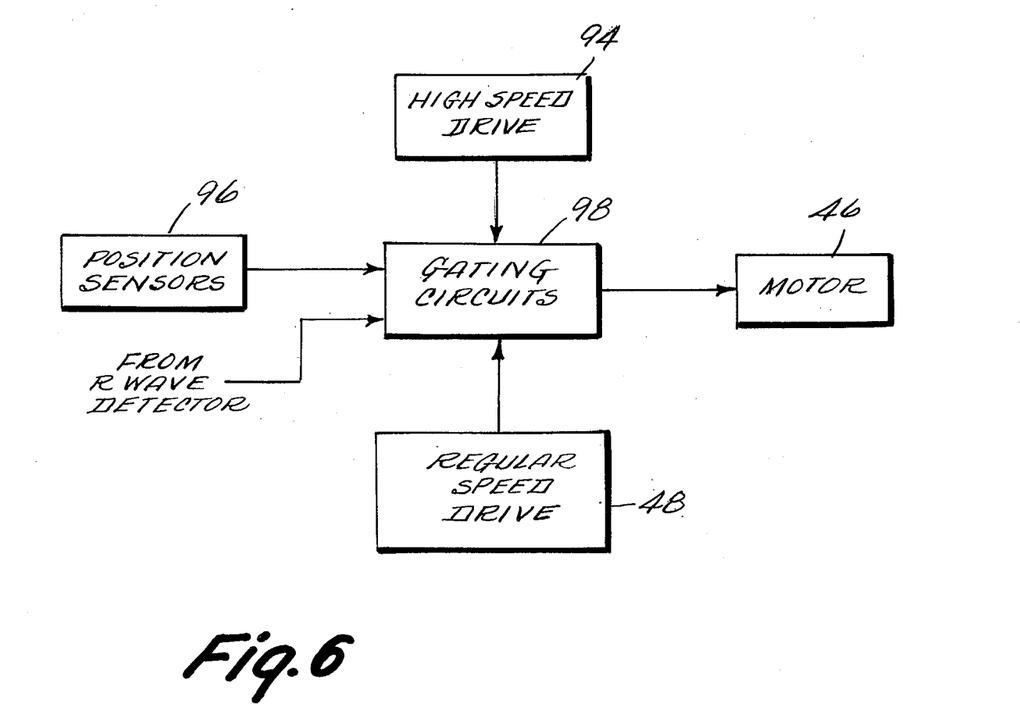
FIG. 6 is a detailed block diagram of alternate embodiment of the present invention showing means for high and low speed driving of the cylindrical record.

Referring now to FIG. 6, there is shown a partial block diagram of an alternate embodiment of the electricardiographic storage system according to the present invention.

In this alternate embodiment, stepper motor drive 48 can be replaced by a high speed stepper motor drive 94 as controlled by one or more position sensors 96. The high speed stepper motor drive 94 is coupled to the output of gating circuits 98 for a predetermined time period whenever position sensors 96 sense the beginning of seam 58. Thus, when seam 58 is sensed, high speed stepper motor drive pulses will be coupled to stepper motor 46 causing it to advance rapidly across the seam. The duration of drive pulses from high rate stepper motor drive 94 is selected so that motor 46 will stop as soon as the entire seam 58 has been traversed. Thus, each time record 18 reaches seam 58, it rapidly traverses the seam and then stops. The next "R" wave triggers the normal recording rotation rate for the drum.

Even further sophistication can be provided by using at least two separate sensors 96. A first "edge start" position sensor detects the leading edge of seam 58 and a second "edge finish" position sensor detects the trailing edge of the seam. The output of edge start and edge finish sensors provide signals to gate circuit 98. Thus, the sensing of the end of seam 58 by the edge finish sensor inhibits further high speed drive pulses from appearing at the output of gate circuits 98. Thus, the output of gate 98 will produce regular speed drive pulses for normal recording each time the "R" wave of a heart beat is detected by threshold detector 26. However, the output will provide high speed drive pulses whenever seam 50 needs to be traversed as indicated by the seam edge start and edge finish position sensors.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method for storing an electrocardiograph (ECG) signal on a rotatable photosensitive record comprising the steps of:

generating an optical signal in response to and representative of the ECG signal;

detecting the presence of a predetermined portion of each ECG signal and generating a synchronization signal responsive thereto;

incrementally rotating the photosensitive record at a predetermined rotational rate for a predetermined period of time in response to each said synchronization signal; and recording said optical signal thereon during said rotating step.

2. A method for storing an electrocardiograph (ECG) signal on a rotatable photosensitive record comprising the steps of:

delaying said ECG signal for a predetermined time;

generating an optical signal in response to said delayed ECG signal;

detecting the presence of a predetermined portion of each ECG signal and generating a synchronization signal responsive thereto;

incrementally rotating the photosensitive record at a predetermined rotational rate for a predetermined period of time in response to each synchronization signal;

recording the optical signal thereon during said rotation step;

detecting a predetermined rotational position of the photosensitive record and generating a position signal responsive thereto; and rotating said record at a predetermined rate for a predetermined period of time in response to said position signal while inhibiting recordation of said optical signal.

3. A method for storing an electrocardiograph (ECG) signal on a rotatable record comprising the steps of:

generating a recordable signal in response to the ECG signal;

detecting the presence of a predetermined wave of each ECG signal and generating a synchronization signal responsive thereto;

incrementally rotating the record at a predetermined rotational rate for a first predetermined period of time in response to each synchronization signal and recording the recordable signal thereon while said record is rotating;

detecting a predetermined position of the record and generating a position signal responsive thereto; and rotating the record at a predetermined rate for a predetermined period of time in response to the position signal while inhibiting the recording of the recordable signal.

4. A method for storing an electrocardiograph (ECG) signal on a rotatable record comprising the steps of:

delaying the ECG signal to produce a delayed ECG signal;

generating an optical signal in response to the delayed ECG signal;

detecting the presence of a predetermined threshold level of each ECG signal and generating a synchronization signal responsive thereto;

incrementally rotating the record at a predetermined rotational rate for a first predetermined period of time in response to each synchronization signal and recording the optical signal thereon while said record is rotating responsive to the synchronization signal;

detecting a first predetermined rotational position of the record and generating a first position signal responsive thereto;

rotating the record at a second predetermined rate in response to the position signal while inhibiting the recording of the optical signal;

detecting a second predetermined rotational position of the record and generating a second position signal responsive thereto; and stopping the rotation of the record in response to the second position signal.

5. Apparatus for storing an electrocardiograph (ECG) signal on a rotatable record comprising:

means for generating an optical signal in response to the ECG signal;

means for detecting the presence of a predetermined wave of each ECG signal and generating a sync signal responsive thereto;

means for incrementally rotating the record at a predetermined rotational rate for a predetermined period of time in response to each sync signal; and means for recording the optical signal thereon while said record is rotating.

6. Apparatus for storing an electrocardiograph (ECG) signal on a rotatable record comprising:

means for generating an optical signal in response to the ECG signal;

means for detecting the presence of a predetermined wave of each ECG signal and generating a sync signal responsive thereto;

means for incrementally rotating the record at a predetermined rotational rate for a predetermined period of time in response to the sync signal;

means for recording the optical signal on said record while said record is rotating;

means for detecting a predetermined rotational position of the record and generating a position signal responsive thereto; and means for rotating the record at said predetermined rate for a second predetermined period of time in response to the position signal while inhibiting the recording of the optical signal.

7. Apparatus according to either of claims 5 or 6 wherein said means for generating an optical signal comprises:

an array of discrete light emitting elements;

converter means coupling said array to said delayed ECG signal for causing predetermined elements of said array to emit light in response to respectively corresponding predetermined levels of said delayed ECG signal;

a lens system for focusing the optical signal onto said rotatable record; and a plurality of optical fibers for coupling the optical outputs of said elements to said lens system in a pattern which causes the physical position of light falling on said record to correspond to the magnitude of said delayed ECG signal.

8. Apparatus for storing an electrocardiograph (ECG) signal on a rotatable record comprising:

means for delaying the ECG signal to produce a delayed ECG signal;

means for generating an optical signal in response to the delayed ECG signal;

first means for detecting the presence of a predetermined threshold level of each signal and generating a sync signal responsive thereto;

first means for incrementally rotating the record at a predetermined rotational rate for a first predetermined period of time in response to each synch signal and recording the optical signal thereon while said record is rotating;

second means for detecting a predetermined rotational position of the record and generating a position signal responsive thereto; and second means for rotating the record at a second predetermined rate for a second predetermined period of time in response to the position signal while inhibiting the recording of the optical signal.

9. A system according to claim 8 wherein said means for generating an optical signal comprises:

an array of discrete light emitting elements;

converter means coupling said array to said delayed ECG signal for causing predetermined elements of said array to emit light in response to respectively corresponding predetermined levels of said delayed ECG signal;

a lens system for focusing the optical signal onto said rotatable record; and a plurality of optical fibers for coupling the optical outputs of said elements to said lens system in a pattern which causes the physical position of light projected onto said record to correspond to said predetermined levels of ECG signal.

10. Apparatus for storing an electrocardiograph (ECG) signal on a rotatable record comprising:

means for delaying the ECG signal to produce a delayed ECG signal;

means for generating an optical signal in response to the delayed ECG signal;

first means for detecting the presence of a predetermined threshold level of each ECG signal and generating a sync signal responsive thereto;

first means for incrementally rotating the record at a predetermined rotational rate for a first predetermined period of time in response to each sync signal and recording the optical signal thereon while said record is rotating;

second means for detecting a first predetermined rotational position of the record and generating a first position signal responsive thereto;

second means for rotating the record at a second predetermined rate in response to the position signal while inhibiting the recording of the optical signal;

third means for detecting a second predetermined rotational position of the record and generating a second position signal responsive thereto; and means for stopping the rotation of the record in response to the second position signal.

11. A system according to claim 10 wherein said means for generating an optical signal comprises:

an array of discrete light emitting elements;

converter means coupling said array to said delayed ECG signal for causing predetermined elements of said array to emit light in response to predetermined levels of said electrical signal;

a lens system for focusing the optical signal onto said rotatable record; and a plurality of optical fibers for coupling the optical outputs of said elements to said lens system in a pattern which causes the physical position of light falling on said record to correspond to said predetermined levels of ECG signal.

12. A system for storing the periodic electrocardiograph (ECG) response of a patient, said system comprising:

means for sensing said ECG response and generating an ECG signal related thereto, said ECG signal including a plurality of wave components for each heart beat;

means for generating an optical signal in response to and representative of said ECG signal;

a substantially cylindrically-shaped record sensitive to said optical signal;

means for focusing said optical signal onto a portion of said record so as to form a spot of light impinging upon said record at a position located along the axial dimension of said record determined by the respectively corresponding magnitude of said ECG signal;

means for incrementally rotating said drum in response to each ECG signal;

means for moving said means for focusing in the axial direction of said record while said record rotates so as to cause a substantially helical trace of said optical spot on said record, said trace including one line for each revolution of said record; and means for synchronizing the rotation of said record with said ECG signal so that corresponding components of a first heart beat of each line of said helical trace are in alignment with one another.

13. A system according to claim 12 wherein said means for generating an optical signal comprises:

an array of discrete light emitting elements;

converter means coupling said array to said ECG signal for causing predetermined elements of said array to emit light in response to predetermined levels of said ECG signal;

a lens system for focusing the optical signal onto said rotatable record; and a plurality of optical fibers for coupling the optical outputs of said elements to said lens system.

14. A system according to claim 12 wherein said means for synchronizing comprises:

a delay line coupled to said ECG signal for producing a delayed ECG signal, said optical signal being generated in response to said delayed ECG signal;

a threshold detector for generating a sync pulse when said ECG signal exceeds a predetermined threshold;

means for rotating said record at a first predetermined rate of rotation for a first predetermined period of time in response to said sync pulse;

means for sensing a predetermined rotational position of said record and generating a position signal responsive thereto; and means for rotating said record at a predetermined rate for a predetermined period of time in response to said position signal.

15. A system according to claim 12 wherein said means for synchronizing comprises:

a delay line coupled to said ECG signal for producing a delayed ECG signal, said optical signal being generated in response to said delayed ECG signal;

a threshold detector for generating a sync pulse when said ECG signal exceeds a predetermined threshold;

means for rotating said record at a first predetermined rate of rotation for a first predetermined period of time in response to said sync pulse;

means for detecting a first predetermined rotational position of said record and generating a first position signal responsive thereto;

means for rotating said record at a second predetermined rate in response to said first position signal;

means for detecting a second predetermined rotational position of said record and generating a second position signal responsive thereto; and means for arresting the rotation of said record in response to said second position signal.

16. A system according to claim 15 wherein said means for generating an optical signal comprises:
an array of discrete light emitting elements;
converter means coupling said array to said delayed ECG signal for causing predetermined elements of said array to emit light in response to predetermined levels of said delayed ECG signal;
a lens system for focusing the optical signal onto said rotatable record; and
a plurality of optical fibers for coupling the optical outputs of said elements to said lens system.

17. A system according to claim 15 wherein said means for synchronizing comprises:
means for sensing a predetermined rotational position of said record; and
means for inhibiting said ECG signal in response to said sensed rotational position for at least a predetermined period of time thereby inhibiting said optical signal for at least said predetermined period of time.

18. A system for storing the periodic electrocardiograph (ECG) response of a patient, said system comprising:
means for sensing said ECG response and generating an ECG signal related thereto;
means for generating an optical signal in response to and representative of said ECG signal;
a substantially cylindrically-shaped drum for receiving a sheet of optically sensitive recording medium wrapped therearound so as to substantially cover the outer surface of said drum thereby forming a seam between the ends of said sheet of recording medium;
means for focusing said optical signal on to a portion of said drum so as to form a spot of light impinging upon said recording medium;
means for detecting a specific component of each ECG signal and for providing an output in response thereto; means for incrementally rotating said drum at a predetermined rate and for a predetermined period of time in response to each output of said means for detecting;
means for moving said means for focusing in the axial direction of said drum while said drum rotates so as to cause a substantially helical trace of said optical signal onto said recording medium, said trace having one line for each revolution of said drum;
means for sensing the leading edge of the seam;
means for rotating said drum in response to said means for sensing the leading edge;
means for sensing the trailing edge of said seam; and
means for arresting the rotation of said drum in response to said means for sensing the trailing edge.

19. A system according to claim 18 wherein said means for generating an optical signal comprises:
an array of discrete light emitting elements;
converter means coupling said array to said ECG signal for causing predetermined elements of said array to emit light in response to predetermined levels of said ECG signal;
a lens system for focusing the optical signal onto said rotatable record; and
a plurality of optical fibers for coupling the optical outputs of said elements to said lens system.

20. In an electrocardiograph storage and display system wherein an ECG signal representing a plurality of heart beats is converted to an optical signal and recorded in a helical track about a rotating recording member, the improvement comprising:
means for defining an index line on the surface of the recording member, said index line running parallel to the axial direction of the recording member and rotating therewith; and
means for incrementally moving said recording member in synchronization with each ECG signal with reference to said index line so that portions of each said signal representing corresponding portions of the heart beats occurring after passage of said index line are recorded at equal respective distances from the index line.

21. A system according to claim 20 wherein said means for synchronizing comprises:
a delay line coupled to said ECG signal for producing a delayed ECG signal, said optical signal being generated in response to said delayed ECG signal;
a threshold detector for generating a sync pulse when each said ECG signal exceeds a predetermined threshold;
means for incrementally rotating said record at a first predetermined rate of rotation for a first predetermined period of time in response to each said sync pulse;
means for sensing a predetermined rotational position of said record and generating a position signal responsive thereto; and
means for rotating said record at a predetermined rate for a predetermined period of time in response to said position signal.

22. A system according to claim 20 wherein said means for synchronizing comprises:
a delay line coupled to said ECG signal for producing a delayed ECG signal, said optical signal being generated in response to said delayed ECG signal;
a threshold detector for generating a synchronization pulse when each said ECG signal exceeds a predetermined threshold;
means for incrementally rotating said record at a first predetermined rate of rotation for a first predetermined period of time in response to each of said synchronization pulses;
means for detecting a first predetermined rotational position of said record and generating a first position signal responsive thereto;
means for rotating said record at a second predetermined rate in response to said first position signal;
means for detecting a second predetermined rotational position of said record and generating a second position signal responsive thereto; and
means for arresting the rotation of said record in response to said second position signal.

23. A system according to claim 20 wherein said optical signal is generated by apparatus comprising:
an array of discrete light emitting elements;

converter means coupling said array to said ECG signal for causing predetermined elements of said array to emit light in response to predetermined levels of said ECG signal;

a lens system for focusing the optical signal onto said rotatable record; and a plurality of optical fibers for coupling the optical outputs of said elements to said lens system.

24. A system according to claim 20 wherein said means for synchronizing comprises:

means for sensing a predetermined rotational position of said drum; and means for inhibiting said ECG signal for at least a predetermined period of time thereby inhibiting said optical signal for a least said predetermined period of time.

25. An electrocardiograph storage system in which an ECG signal is recorded on a rotating recording member comprising:

means for generating an optical signal related to said ECG signal;

means for focusing the optical signal onto the surface of the recording member while the recording member is rotating; and means for moving the point of focus of the optical signal in the axial direction of the recording member while the recording member is rotating to produce a helical trace optical exposure of the rotating recording medium;

wherein said means for generating an optical signal comprises an array of discrete light emitting elements;

analog-to-digital converter means coupling said array to said ECG signal for causing predetermined individual elements of said array of emit light in response to respectively corresponding predetermined levels of said ECG signal; and a plurality of optical fibers for coupling the optical outputs of said elements to said means for focusing.

* * * * *